United States Patent [19]

Jöbsis

[11] Patent Number: 4,805,623
[45] Date of Patent: Feb. 21, 1989

[54] SPECTROPHOTOMETRIC METHOD FOR QUANTITATIVELY DETERMINING THE CONCENTRATION OF A DILUTE COMPONENT IN A LIGHT- OR OTHER RADIATION-SCATTERING ENVIRONMENT

[75] Inventor: Frans F. Jöbsis, Efland, N.C.

[73] Assignee: Vander Corporation, Efland, N.C.

[21] Appl. No.: 93,482

[22] Filed: Sep. 4, 1987

[51] Int. Cl.⁴ .......................................... G01N 33/48
[52] U.S. Cl. .................................. 128/633; 250/339; 356/41; 356/320
[58] Field of Search ............... 128/632, 633, 664, 666; 356/40, 41, 320; 250/339

[56] References Cited

U.S. PATENT DOCUMENTS

| | | | |
|---|---|---|---|
| 3,790,797 | 2/1974 | Sternberg et al. | 21/26 |
| 3,825,342 | 7/1974 | Lubbers et al. | 356/41 |
| 4,086,915 | 5/1978 | Kofsky et al. | 128/2 L |
| 4,114,604 | 9/1978 | Shaw et al. | 128/2 L |
| 4,166,454 | 9/1979 | Meijer | 128/666 |
| 4,167,331 | 9/1979 | Nielsen | 356/39 |
| 4,223,680 | 9/1980 | Jöbsis | 128/633 |
| 4,281,645 | 8/1981 | Jöbsis | 128/633 |
| 4,299,487 | 11/1981 | Sengoku et al. | 356/320 |
| 4,407,290 | 10/1983 | Wilbur | 128/633 |
| 4,427,889 | 1/1984 | Muller | 250/339 |
| 4,446,871 | 5/1984 | Imura | 128/633 |
| 4,467,812 | 8/1984 | Stoller | 128/664 |
| 4,509,522 | 4/1985 | Manuccia et al. | 128/634 |
| 4,623,248 | 11/1986 | Sperinde | 356/41 |
| 4,629,322 | 12/1986 | Pollard | 356/300 |
| 4,651,741 | 3/1987 | Passafaro | 128/633 |
| 4,655,225 | 4/1987 | Dähne et al. | 128/633 |
| 4,697,593 | 10/1987 | Evans et al. | 128/634 |
| 4,707,603 | 11/1987 | Miemela et al. | 250/339 |
| 4,714,080 | 12/1987 | Edgar et al. | 128/633 |

OTHER PUBLICATIONS

"Scanning The Brain With Light", *Popular Mechanics*, p. 66, Nov. 1987.

Primary Examiner—William E. Wayner
Attorney, Agent, or Firm—Steven J. Hultquist

[57] ABSTRACT

A spectrophotometric method is described of quantitatively determining the concentration of a dilute component in either a clear or a strongly light-scattering environment containing same in unknown concentration together with a reference component of known concentration, by a series of contemporaneous radiation-directing and measurement steps of radiation of selected varying wavelengths. Specific applications are disclosed involving the in situ, in vivo, non-invasive spectrophotometric determination of blood-borne as well as tissue species, e.g., hemoglobin, and oxyhemoglobin, and intra-cellular enzyme cytochrome c oxidase, in human body parts such as fingers, hands, toes, feet, earlobes, etc., as well as organs such as the brain, skeletal muscle, liver, etc.

23 Claims, 3 Drawing Sheets

SPECTROPHOTOMETRIC METHOD FOR QUANTITATIVELY DETERMINING THE CONCENTRATION OF A DILUTE COMPONENT IN A LIGHT- OR OTHER RADIATION-SCATTERING ENVIRONMENT

BACKGROUND OF THE INVENTION

1. Field of the Invention

This invention generally relates to a spectrophotometric method of quantitatively determining the concentration of a dilute component in a light- or other radiation-scattering environment containing the dilute component in combination with a reference component of known concentration.

2. Description of the Related Art

In many fields of technology there is a need for quantitative determination of dilute component concentrations in environments where the dilute component is in combination with a reference component of known concentration. Examples of illustrative environments of such type include enzymes, proteins, and metabolites in corporeal fluids; acidic fumes or gaseous components (e.g., hydrogen sulfide and sulfuric acid, nitric acid, carbon monoxide, etc.) in the atmosphere; salt concentrations in sea water undergoing desalination; ozone in ozone-enriched air utilized in waste water ozonation systems, etc.

In particular, there has been a specific need in the medical and health care fields for a non-invasive, continuous, atraumatic, in vivo, in situ determination of amounts of critical metabolic indicators in body fluids or tissues of human patients. Examples of such body fluids include the blood and fluids associated with the lymphatic and neurological systems of the body. Further specific examples involving the human circulatory system include the monitoring of glucose and of oxygenated/de-oxygenated, arterial/venous colored hemoglobin in the blood stream. In addition, monitoring in localized tissue, such as brain and muscle, of certain enzyme species such as the cytochrome c oxidase enzyme (unofficially better known as cytochrome a, $a_3$) or metabolic substrates (such as glucose) or products (such as carbon dioxide) is becoming an increasingly urgent practical application of spectrophotometric technology.

Spectrophotometric methods have been proposed in the art to monitor metabolites in corporeal fluids. Such methods involve the impingement of radiation, typically in the visible or near-infrared region, onto the exterior body portion of the subject for transdermal and interior tissue penetration of the radiation, which is monitored as to its reflectance or transmission, at a wavelength condition at which the metabolite or other monitored component is selectively absorptive for the radiation. This technique is mainly limited to yielding a qualitative determination from the measured output radiation (reflected or transmitted) of the qualitative character of the metabolism. At best a semi-quantitative result can be obtained in a so-called trend monitoring mode where concentration changes can be monitored in terms of an original baseline condition of unknown concentration.

Solute concentrations in dilute fluid media can be theoretically quantified by the Beer-Lambert law, i.e., $$\log(I_0/I) = d \times E \times c$$

wherein:

$I_0$ = intensity of source radiation impinged on the sample;

$I$ = intensity of radiation transmitted through the sample;

$E$ = absorption (extinction) coefficient of the solute species at the wavelength of the source radiation impinged on the sample;

$d$ = optical distance (travel pathlength of the radiation transmitted through the sample); and $c$ = concentration of the solute (dilute component) in the solution sample.

Although the foregoing Beer-Lambert Law equation permits a ready determination of solute concentration to be made in in vitro or other non-corporeal discrete sample systems utilized for conventional spectrophotometric assays, such direct, quantitative measurement is not possible in the intact body, even though the influent radiation is penetrative of the body elements of the corporeal system, e.g., bones, musculature, organs, and the like, since the scattering of radiation during its passage through the corporeal system is extensive and highly variable in character. Such scattering not only adds an unknown loss of radiation to the required information regarding specific absorption but by multiple scattering it also lengthens to an unknown degree the path length of those photons eventually emerging from the body element. As a result, it has not been possible to determine in an in vivo situation what the effective path length, $d$, of the impinged radiation actually is, prior to measurement of the transmitted or reflected radiation derived therefrom. In consequence, the absolute quantitation of solute concentrations in corporeal systems has been severely adversely limited.

Faced with the alternatives of invasive and traumatic sampling of the corporeal fluids of interest, or spectrophotometric methods which realize only qualitative or at best semi-quantitative measurement of changes in tissue or body fluid solute concentrations, there is a substantial perceived need in the art for a non-invasive, in vivo method of quantitatively determining the concentration in corporeal solution of a solute in a body fluid solvent.

A similar need exists in numerous other fields in which absolute concentrations of dilute component species in fluid media would materially assist the characterization of the fluid system. An example is atmospheric monitoring of "acid rain", i.e., airborne acidic contaminants which have in recent years proliferated and been determined to cause widespread biospheric damage, including the defoliation of forest stocks and spoliation of natural bodies of water and other aqueous environments. It is anticipated that in coming years with the increasing severity of the acid rain problem, correspondingly greater scientific and legislative efforts will be focused on the monitoring of acid rain with a view to controlling and minimizing its adverse impacts. Determinations in the naturally existing medium such as turbid water and hazy or cloudy atmosphere will be a great boon for direct, effective and rapid monitoring of these environments.

In numerous other industrial and natural systems there is a need to quantitatively monitor solute species in an indirect manner not involving the time, effort, and cost of discrete sample collection, purification and analysis.

U.S. Pat. No. 4,281,645 to F. F. Jöbsis describes a spectrophotometric system for monitoring cellular oxidative metabolism by non-invasively measuring in vivo changes in the steady state oxidation-reduction of cellular cytochromes together with changes in blood volume, the oxidation state of hemoglobin and the rate of blood flow in the brain, heart, kidneys, other organs, limbs, or other parts of a human or animal body.

The methodology described in the Jöbsis patent involves transmitting near-infrared radiation in at least two different and periodically recurring wavelengths through the corporeal environment, and detecting and measuring the radiation intensity which emerges at another, distant point or on the opposite side of the body, for the monitoring of biochemical reactions, utilizing an approximation of the Beer-Lambert law. One of such wavelengths selected for the measurement is in a range for which oxidized cytochrome a, $a_3$, is selectively highly absorptive. One or more reference signals are provided at corresponding wavelengths outside the peak of the cytochrome absorption band but preferably in close proximity to the measuring wavelength. The difference or ratio between the measuring and reference signals is determined and non-specific changes in the intensity of transmitted radiation not attributable to absorption by the cytochrome species are eliminated. Thus, the system of this patent produces an output signal representing the difference in or ratio of absorption of the measuring and reference wavelengths by the organ or other corporeal portion of the body as a function of the state of the metabolic activity in vivo, which may be converted to a signal providing a substantially continuous measure of such activity. A related spectrophotometric reflectance technique is disclosed in U.S. Pat. No. 4,223,680 to F. F. Jöbsis.

U.S. Pat. No. 4,655,225 to C. Dähne et al discloses a spectrophotometric system for non-invasive determination of glucose concentration in body tissue. The system involves irradiation of the exterior body portion with an optical light whose transmittance or reflectance is collected at selected band wavelength values for the glucose absorption spectrum and at a selected band wavelength value for the absorption spectrum of background tissue containing no or insignificant amounts of glucose. The measuring and reference radiation collected is then converted into electrical signals and utilized to determine glucose concentrations.

It is an object of the present invention to provide an improved method and apparatus for indirectly quantitatively, spectrophotometrically determining the amounts of a dilute component by using a reference component in the environment of interest.

It is another object of the invention to provide such a method for non-invasive, in vivo quantitative determination of the concentration of a dilute solute component in a corporeal solvent environment.

Other objects and advantages of the present invention will be more fully apparent from the ensuing disclosure and appended claims.

SUMMARY OF THE INVENTION

The present invention relates to a method of determining the true concentration (e.g., in terms of grams or moles of a dilute component per volume of a reference component) in environmental media in which the optical pathlength is ill-defined due to the extensive occurrence of scattering of incident radiation, such as in very long distance atmospheric monitoring as well as in more intensely light scattering media during transillumination as well as diffuse reflectance modes of spectrophotometry.

As used herein, the term "environment" refers to a selected spatial region in which the directed and measured radiation is transmitted and/or reflected along substantially the same path.

The crux of the invention is to measure the transmitted and/or reflected radiation for both the dilute component of unknown concentration and the reference component of known concentration with which it is associated. Multiple scattering spoils the optical pathlength parameter in the Beer-Lambert equation and does so to different degrees depending on the wavelength. It is, therefore, necessary to measure the dilute and reference components in closely the same spectral region. Measuring the intensity of the light absorption and/or reflectance by the two types of molecules, dilute component and reference component, in the environment and applying the extinction coefficients of each provides the opportunity to relate them to one another in terms of relative amounts, which is recognized as being the essential character of concentration. Thus, by absorption (and/or reflectance) measurements and with knowledge of the extinction coefficients, the amount of dilute component in the light path and the amount of reference component it is associated with, determined similarly at other near-by wavelength(s), may be employed to calculate the concentration of the dilute component relative to the reference component.

In a system in which the reference component is present in known concentration, the apparent pathlength may be determined by absorption measurements taken in the environment of unknown pathlength in the same electromagnetic spectral region. The difference between the resulting absorption values is calculated as the differential absorbance in the environment whose pathlength is to be determined. The tabulated or previously determined extinction coefficient values of the pure reference component at such wavelengths are then employed to calculate the differential extinction coefficient, as the difference between the respective extinction coefficient values. When the differential absorbance is then divided by the differential extinction coefficient, the result is the apparent effective pathlength of the environment. When the electromagnetic radiation emitter and detector spacing distance is measured, the pathlengthening factor for the system is determined as the ratio of the apparent effective pathlength to the actual emitter-to-detector spacing distance.

In another selected, specific aspect, the invention relates to a spectrophotometric method of quantitatively determining the concentration of a dilute component in an environment containing the dilute component of known identity but of unknown concentration in combination with a reference component of known concentration, by a series of successive, substantially contemporaneous measurements of transmitted and/or reflected radiation at selected wavelengths, comprising:

(a) determining the apparent effective pathlength in said environment;

(b) directing at the environment incident electromagnetic radiation of a first wavelength in a selected spectral region at which the dilute and/or reference component(s) exhibit absorption for the electromagnetic radiation;

(c) measuring the first wavelength radiation transmitted and/or reflected by the environment;

(d) directing at the environment incident electromagnetic radiation of at least one other wavelength in the selected spectral region at which the dilute and/or reference component(s) exhibit absorption of different relative intensities than for the first wavelength incident radiation, whereby absorption is exhibited in said selected spectral region comprising said first and at least one other wavelength by both the dilute and the reference component(s);

(e) measuring the other wavelength radiation transmitted or reflected by the envinroment; and (f) determining extinction coefficient values for the dilute component at said first and other wavelengths in said environment; and (g) based on the apparent effective pathlength determined for the environment, extinction coefficient values for the dilute component at said first and other wavelengths, and the measured absorbed and/or reflected radiation at said wavelengths, determining the relative amount of the dilute component to the amount of the reference component, as the concentration of the dilute component in the environment.

In another aspect of the method broadly described above, the determination of step (f) is effected by establishing simultaneous modified Beer-Lambert equations for each of the radiation absorption and/or reflectance measurement steps, and solving the equations for the concentrations of the dilute component and the reference component in the environment.

A further aspect of the invention relates to a spectrophotometric method of quantitatively determining the concentration of a dilute component in an environment containing the dilute component of known identity but of unknown concentration in combination with a reference component of known concentration, comprising:

(a) directing at the environment incident electromagnetic radiation at a number of wavelengths in a selected spectral region at which the dilute and/or reference components exhibit absorption for the electromagnetic radiation, the number of such wavelengths being determined by the number of dilute and reference components in the environment, and the scattering characteristics of the environment;

(b) determining the absorbance of the environment of the electromagnetic radiation at the various wavelengths and the relative intensities of the absorption contributions of the dilute and reference components and scattering losses from the environment at each of such wavelengths;

(c) at each of such wavelengths, establishing absorption equations of the form:

$$Abs_w = \sum_{i=1}^{n} x_i A_i + zR + S,$$

wherein: $Abs_w$ is the absorbance by the environment, containing the dilute and reference components, of the incident electromagnetic radiation of wavelength w; $x_i$ is the relative intensity of the absorption contribution of the associated dilute component $A_i$, and wherein terms of the form $x_i A_i$ are set forth for each of the dilute components; n is the number of dilute components; z is the relative intensity of the absorption contribution of the reference component; R is the concentration of the reference component; and S is the normalized scattering of the environment at wavelength w, thereby establishing for each of such wavelengths an absorbance equation, to yield a set of simultaneous equations whose number equals the number of dilute and reference components and the number of wavelengths required to characterize the scattering of the environment;

(d) deriving algorithms by matrix solution of the aforementioned simultaneous equations, said algorithms being of the form:

$$[c] = \sum_{i=1}^{m} a_i Abs_{wi},$$

wherein: [c] is the concentration of the specific dilute or reference component, $a_i$ is a determined numerical constant; m is the number of said wavelength determinations; and $Abs_{wi}$ is the absorbance at wavelength w, thereby establishing the concentration of each of the dilute and reference components in the environment.

In the above described method aspects of the invention for quantitatively determining the concentration of the dilute component in the environment containing same in combination with a reference component of known concentration, the various radiation-directing and measuring steps at the various selected wavelengths will be carried in a contemporaneous fashion to determine the dilute component concentration. It will be recognized, however, that in many systems of interest, especially including corporeal environments, it may be desirable to establish the dilute component concentration by such contemporaneous radiation-directing and measurement steps, and that subsequent to such determination, it may be advantageous to monitor the system for a period of time, either at discreet intervals or on a continuous basis.

Still another aspect of the invention relates to apparatus for spectrophotometrically quantitatively determining the concentration of a dilute component in an environment containing the dilute component of known identity but of unknown concentration in combination with a reference component of known concentration, comprising:

(a) means for producing electromagnetic radiation of known wavelengths and directing said radiation into the environment to be characterized for the dilute component;

(b) means for detecting electromagnetic radiation emanating from and/or reflected from the environment and producing therefrom an electrical signal corresponding thereto;

(c) means for receiving said electrical signal and producing therefrom electrical signals at corresponding to said different wavelengths;

(d) means receiving and operatively responsive to said electrical signals corresponding to said different wavelengths, to establish absorbance equations responsive to said electrical signals corresponding to said different wavelengths, wherein absorbance at each of the wavelengths is expressed as a function of the relative intensities of the absorption contributions of the dilute and reference components and the concentrations of the dilute and reference components, and for calculating the amounts of the absorbing species by solution of said absorbance equations; and (e) means for displaying the calculated concentrations of said dilute and reference components.

In general, the number of wavelengths employed for concentration determination of the dilute component(s) in the system will be equal to the number of absorbing species (i.e., the number of dilute component(s) and the reference component). If the environment exhibits a flat non-specific baseline for background scattering due to wavelength independent scattering, an additional one wavelength must be added, while if the baseline is linearly sloped an additional two wavelengths must be introduced, and if the scattering is non-linearly wavelength dependent, a number of extra wavelengths will be required to correct for the curvature of the baseline, with increasing wavelength determinations providing increased accuracy to the determined concentrations.

In another aspect of the invention, in instances where an absorption band of the reference component is not present in the spectral region in which the selected dilute component (i.e., the dilute component whose concentration is desired) has its absorption spectra, but such spectral region contains a band of a second dilute component, and a relatively near near spectral region exists in which the reference component and the second dilute component exhibit absorption, the concentration of the second dilute component may be determined and used as a bridging reference for determination of the selected dilute component concentration by calibration of the selected dilute component against the second dilute component.

Applications of the present invention extend to the entire field of analytical chemistry utilizing a spectrophotometric means to determine concentrations in radiation scattering circumstances. Special attention shall be given in the following description to applications in the bio-medical field of non-invasive monitoring of metabolism.

One of these bio-medical applications is the determination of the oxidation-reduction state of enzymes and the degree of oxygenation of the blood flowing through actively metabolizing solid organs such as the brain, skeletal muscle, the liver, etc. An optical reflectance technique is used when such organs are too large for effective transillumination. Such measurements provide much needed diagnostic information on the adequacy of oxygen delivery and oxygen utilization to vital organs at any moment in time and on an on-going basis.

A second preferred application using a transillumination mode is the measurement of hemoglobin content in blood by the quantitative determination of the hemoglobin and water content of the pulsatile increases in blood content of a finger or earlobe as it pulsates with each heartbeat. Measurements can similarly be made of other blood-borne constituents (e.g. glucose, lipids, cholesterol, carbon dioxide, etc.) that possess absorptive characteristics in the invisible, infrared or other parts of the electromagnetic spectrum.

In other general applications of the present invention, quantitative determinations can be made in light- or other radiation-scattering media, mixtures, or solutions, of any and all constituents possessing absorption characteristics in a spectral range in which a reference compound of known concentration also possesses significant absorption characteristics. Such applications are not limited to the visible or near infrared parts of the spectrum but can be performed in any part of the electromagnetic spectrum in which absorption of the radiation in either a transillumination or in a reflective mode is not so intense as to preclude the acquisition of a radiation signal strong enough for routine instrumental analysis.

Figure 1:
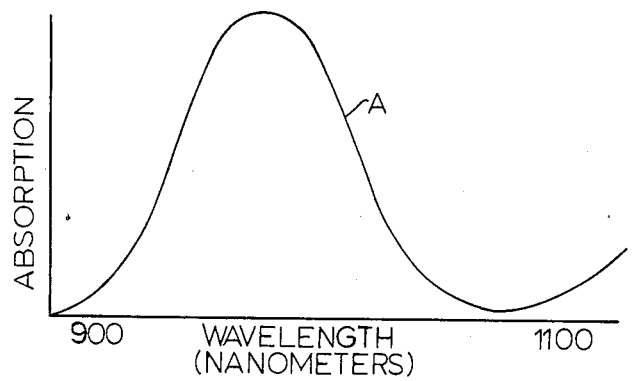
FIG. 1 is a plot of the absorption spectrum of pure component water.

DETAILED DESCRIPTION OF THE INVENTION, METHODOLOGY, AND PREFERRED EMBODIMENTS THEREOF

The present invention not only remedies the shortcomings of prior art infrared monitoring techniques but more generally provides a method to ascertain the concentration of a spectrophotometrically absorbing material under conditions where the pathlength of the light beam is unknown. This uncertainty exists in any light scattering medium, be it a liquid, a solid, or a gaseous mixture, in which multiple scattering lengthens the geometrically measurable optical pathlength. The present invention overcomes this problem of undefined pathlength in media which have light-absorbing properties of their own in the electromagnetic radiation spectral region of the wavelength range in which the material whose concentration is to be determined is radiation absorptive.

The general broad applicability of the invention will be clear from the ensuing description of the invention, even though this description utilizes the near infrared spectral range in the illustrative examples hereinafter set forth. It should also be noted that in a spectral range (e.g., the visible range) in which the solution or any other known component does not absorb the impinged radiation, an indicator may in some instances be desirably added (specifically in in vitro determinations) to the solution to establish the effective pathlength traversed by the photons.

The Beer-Lambert law defines the basis of the spectrophotometric determinations of concentrations of radiation absorbing materials. It emphasizes that the absorption of light (or other radiation) depends on just two conditions: the efficiency of the molecules or atoms to absorb light and the number of such molecules or atoms in the light path. Two aspects should immediately be noted. The efficiency of radiation absorption varies at different wavelengths making it necessary to use a narrow "monochromatic" band of light and to state the efficiency with which the material absorbs that light. This parameter is called the extinction coefficient. The other aspect is the consequence that when the length of the light path through the selection or mixture is known, the only variable determining the number of molecules or atoms in the solution or mixture is the concentration. The entire field of quantitative analysis using bench-top spectrophotometers applies this fact by using spectrophotometric vessels ("cuvettes") of known pathlength dimensions. Of course, clear solutions or gas mixtures are required in such analysis to avoid lengthening of the optical pathlength by multiple light scattering. Scattering media are also avoided whenever possible because the light lost by scattering complicates the determination of light lost by absorption. Differential spectrophotometry has been developed to decrease errors due to mild scattering where light losses may occur but where pathlengthening is still a negligible factor. This technique employs either two closely spaced monochromatic wavelengths with different absorption coefficients, or two samples with equal light-scattering properties but one lacking the absorbing material to be determined. It should be emphasized that these two well-known approaches to differential spectrophotometry can not, and do not, correct for optical pathlengthening by scattering.

The Beer-Lambert law for solutions states that the logarithm of the fraction of the light absorbed by the dissolved material (the solute) equals the molar extinction coefficient (E) of the solute times the concentration (c) times the pathlength (d); or, as rewritten to determine an unknown concentration:

$$c = 1/E \cdot 1/d \cdot \log I_o/I$$

The quantity $\log I_o/I$ is called the Absorbance (formerly the Optical Density). In these equations $I_o$ is the original intensity of the light without an absorbing species and I the intensity after the beam has traversed the solution. In practice the intensity $I_o$ is defined as the light falling on the detector of the spectrophotometer after it has traversed a cuvette containing pure solvent. The signal thus obtained is designated Io and the signal obtained with an identical cuvette containing the solution of unknown concentration is designated I.

The extinction coefficient is standardly given in the form of the amount of absorption produced over a 1 cm pathlength by a 1 molar solution (one molecular weight of solute contained in one liter of solution). Values for molar extinction coefficients are commonly available in published tables and are usually given for wavelengths of maximal absorption.

Transillumination of a material with intense light-scattering properties results in a significant fraction of photons falling on the detector having had a tortuous pathway that increased the distance traversed beyond the direct geometric length of the sample. In the most extreme mode, viz., reflectance spectrophotometry, absorbance spectra are taken utilizing the photons scattered out of the sample, either obliquely (typically 90° angle observation) or back-scattered (same surface observation). Not only is the pathlength then unknown it is undefined especially in the case of same surface observations. The mean depth of penetration before back scattering occurs is difficult or impossible to determine. In either case the effective pathlength is unknown and concentrations can not be determined by the Beer-Lambert law.

The present invention substitutes a totally new approach to determine concentrations in various media—solutions, gas mixtures, and solids—an approach not predicated on pathlength but on simultaneous measurement of the amount of medium traversed. In solution this method provides therefore a statement concerning the amount of solvent encountered. From this parameter and the strength of absorption by the solute, the concentration of the solution can be derived. A prerequisite is that the absorption bands occur at relatively closely-spaced wavelengths, scattering being wavelength dependent, especially in the visible and ultraviolet wavelengths regions of the spectrum.

FIG. 1 shows the absorption spectrum of pure component water over a selected spectral region in the wavelength range of approximately 900–1100 nanometers. In a non-scattering environment containing only the reference component, the concentration of that component can be determined if the pathlength is known as is done in routine benchtop spectrophotometry. Conversely, if the concentration is known but the pathlength unknown the latter can be calculated instead, as should be clear from inspection of the Beer-Lambert law.

The absorbing component of FIG. 1 can be either an indicator or the solvent itself. For ease of understanding it is instructive to consider the absorbing component to be an indicator. Such indicator must be present in known concentration. If an appropriate indicator component is lacking in the spectral range of the experiment, a suitable indicator which is absorptive in the spectral range of interest can be added to the solution at a known concentration. What also must be known is the molar extinction coefficient of the indicator per centimeter pathlength at the measuring wavelength. Intensity of the measured absorption peak then indicates the length of the optical path. This indicator technique, although useful in bench top spectrophotometry, does clearly not lend itself well to in vivo monitoring. In that situation, however, the ubiquitous presence of water in biological tissues makes water the indicator of choice, just as in atmospheric applications nitrogen gas can fill this need.

It is relevant to point out that it is possible to express water in terms of its own concentration, which then provides a case formally identical to the indicator case above. Concentrations are often expressed either in grams per liter but more stringently in terms of molarity, i.e., moles per liter of solution which means $$\frac{\text{grams}}{\text{molecular weight}} \text{ per liter.}$$

Since the weight of a liter of water is 1000 grams and its molecular weight is 18, pure water exists in the form of of 1000/18=55.6 molar "solution." Thus water is an indicator present at known concentration. However, in terms of the present discussion it is clarifying to note, for the special case of water or any other spectrophotometrically measurable solvent, that if it is known that a 1 cm cuvette filled with pure water shows an Absorbance of say 0.50 at a given wavelength, then an Absorbance value of 6.00 found at that same wavelength over an unknown pathlength shows that that pathlength must have been 12 cm.

In this discussion, it may also be noted that the solute molecules do displace water molecules to a certain extent, lowering thereby its concentration in the solution as compared to its own concentration in pure water. This effect is, however, very small for the dilute solutions encountered in most situations. For example, the most concentrated salt component of blood (NaCl) produces a less than 2.6 ml increase in volume when dissolved in a liter of water. Therefore, the water content of the resulting "physiological salt solution" is decreased by less than 0.26%. The errors thus created are far smaller than many uncertainties inherent in this or any other spectrophotometric methodology.

The parallel argument for the macro-molecular and so-called "formed" components of tissues, however, is best reduced to terms of water content. Typically, for soft tissues the water content is 85% percent. A correction of about 15 to 20% is significant and could be applied in such cases. In that case the determined concentrations would be in terms of total tissue mass. This may, however, not be preferable to an expression in terms of total tissue water which would result if the 15 to 20% correction is not applied. It might be noted here that an identical approach is applicable to the analysis of gaseous mixtures that exhibit light scattering, i.e. such as haze, steam, or clouds. For many atmospheric applications, nitrogen gas can serve as the reference component at known concentration, i.e., approximately 79%. Altitude or changes in barometric pressure do not decrease its usefulness since the $N_2$ percentage will remain the same and a contaminant can still be determined in terms of percent, per mil or parts per million.

The above examples, referring to FIG. 1, are based on totally clear, i.e., non-scattering, solutions or mixtures allowing a single wavelength approach. When scattering occurs, we must correct for light losses not related to absorption and for pathlengthening due to multiple scattering. When several components produce overlapping absorption spectra this adds to their complexity. In the following four cases, light scattering and absorption situations of increasing complexity will be analyzed.

Figure 2:
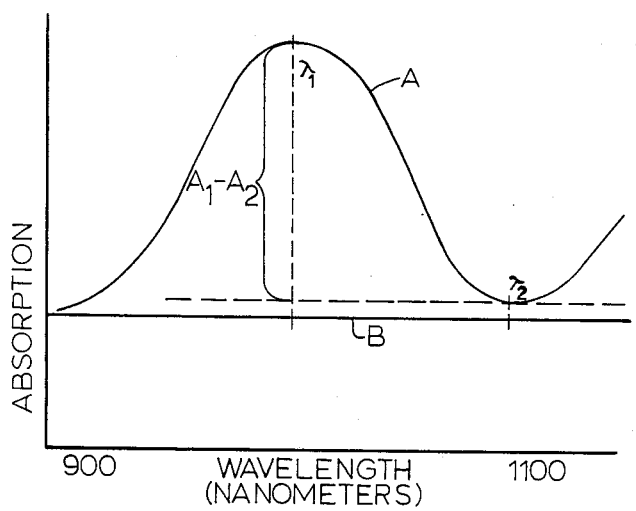
FIG. 2 is a plot of the absorption spectrum of water in an environment exhibiting a flat baseline, B, associated with radiation scattering.

In FIG. 2 the case for wavelength independent scattering is illustrated. Light loss, equal throughout the relevant range of the spectrum, creates a "baseline shift" (identified by line B in FIG. 2) which adds to the spectrum of the material to be determined (water in this example). A two wavelength differential approach is now indicated as the first, minimal step to cope with the problem. It amounts to subtracting signals at two wavelengths ($\lambda_1$ and $\lambda_2$) thereby eliminating the light lost by scattering.

For the spectrum of water in the wavelength range of 900–1100 nanometers, the extinction coefficients of water at two points along the wavelength range, e.g., at 980 and 1100 nanometers may be readily determined or obtained from tabulated values for the pure water component. The difference in the observed Absorbance values at these respective wavelengths is a measure of either the amount of water encountered by the photon stream along their optical path, or in the case of a dilute solution (i.e., a solution in which the water concentration remains approximately 55.6 molar) a measure of the pathlength. Therefore, if the actual differential Absorbance, i.e., the difference in absorption values at the wavelength values of 980 and 1100, nanometers is determined, the effective pathlength of the test system can be derived by dividing the measured differential absorbance by the differential absorbance value between 980 and 1100 nanometers for 1 cm of water.

For example, FIG. 2 shows the absorption spectrum for water (curve A), over the spectral range of from about 900 to about 1100 nanometers, with a flat baseline attributable to environmental scattering (baseline B). The plot shows the peak of the absorption spectrum for water (curve A) at a first wavelength, $\lambda_1$, and a trough in the spectrum at a second wavelength $\lambda_2$. The difference in absorption for water at the respective $\lambda_1$ and $\lambda_2$ values is indicated by the quantity $A_1 - A_2$, as the differential absorption in an environment exhibiting background scatter producing a flat baseline. The practice of subtracting absorption signals at adjacent wavelength values in this manner, where the known component differs significantly in its absorbance at the respective wavelengths, amounts to subtracting an existing wavelength-independent baseline of loss by scattering. The intensity of the remaining $A_1 - A_2$ value provides a measure of the effective pathlength. What has not yet been discussed is the determination of the concentration of other absorbing components dissolved in the water and their effect on the water measurement.

Figure 3:
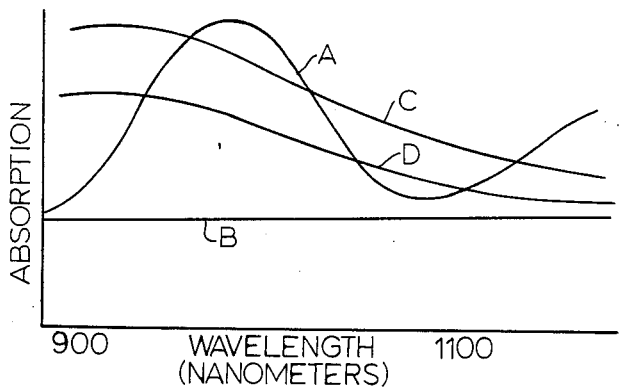
FIG. 3 is a plot of the absorption spectra of water, hemoglobin, and oxyhemoglobin, with a flat baseline attributable to radiation scattering by the environment.

FIG. 3 shows absorption spectra for water (curve A), oxyhemoglobin (curve C), and de-oxyhemoglobin (curve D), against a flat baseline (curve B) associated with scattering losses in the system. The derivation of the effective pathlength through the sample in the FIG. 3 system is more complex since other absorption curves occur in the spectral range needed to determine the amount of the "known" or "reference" material (i.e., water). For three absorbing species (water, hemoglobin, and oxyhemoglobin), a minimum of three wavelengths is required so that three absorbance equations or "algorithms" can be established and solved for the unknowns, i.e., the contributions of the three absorber species. If a flat non-specific baseline exists (due to wavelength-independent scattering, as shown), a fourth wavelength must be added, to yield four equations to solve for the four unknown contributions. Solution of these four equations provides information on the amount of each material encountered. The known concentration of water (55.6 Molar) provides the opportunity to calculate the pathlength that must have been traversed and thereby enables the calculation of the concentration of the other components. In simplified terms, this can also be done by calculating the apparent effective pathlength from the water signal and deriving the concentration of the solute(s) in this manner.

Figure 4:
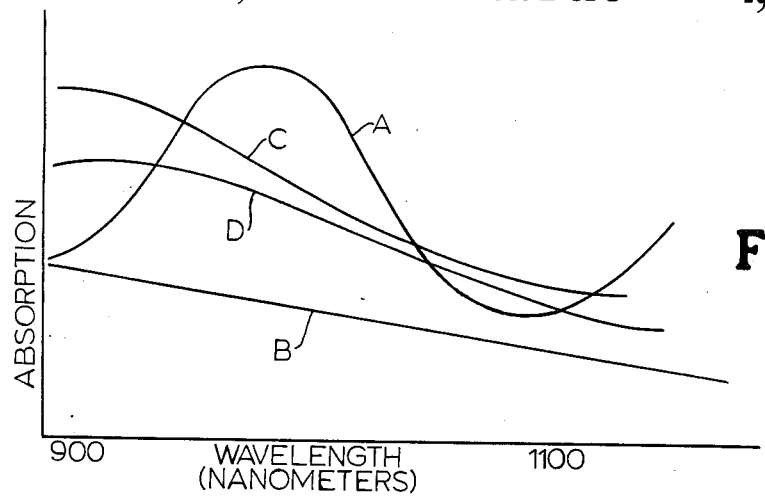
FIG. 4 is a plot of the absorption spectra of water, hemoglobin, and oxyhemoglobin, with a linearly sloped baseline for wavelength-dependent radiation scattering in the environment.

A similar type of complexity is produced by scattering that varies in intensity as a function of wavelength over the spectral region considered. FIG. 4 is a plot of absorption spectra for water (curve A), oxyhemoglobin (curve C), and de-oxyhemoglobin (curve D), against a linear, sloped baseline (curve B). In absorption systems of this type, a fifth wavelength must be introduced in the absorbance relationships to determine the degree of steepness of the slope.

Figure 5:
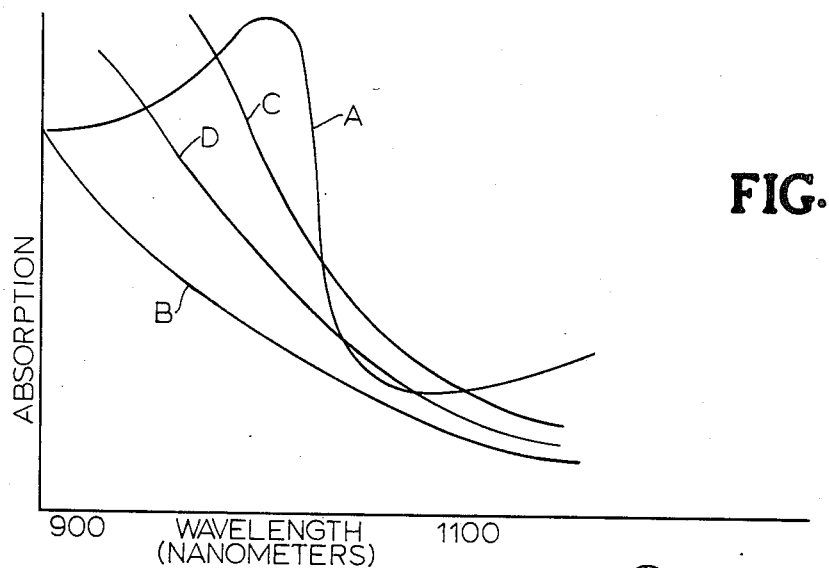
FIG. 5 is a plot of the absorption spectra of water, hemoglobin, and oxyhemoglobin, with a curved baseline evidencing wavelength-dependent radiation scattering in the environment.

In systems of the type shown in FIG. 5, wherein the water, oxyhemoglobin, de-oxyhemoglobin, and baseline curves are denoted by the letters A, C, D, and B respectively, and wherein the baseline indicates scattering of a curvilinear wavelength-dependent character, a number of extra wavelengths will be required to correct for the curvature of the baseline. The higher the degree of accuracy required for the calculated concentrations, the greater the number of wavelength determinations that must be employed.

METHODOLOGY

The method of the present invention has particular applicability to the determination of concentrations of blood components, such as the aforementioned hemoglobin and oxyhemoglobin, in body extremities where transillumination is employed, i.e., a source of radiation is impinged on the body part and collected at another exterior region of such body part. This methodology is applicable to body parts such as fingers, toes, earlobes, and other organs up to and including infants' heads. Alternatively, reflectance spectrophotometry may be employed in portions of the body where transillumination is impractical due to the mass and optical density of the body part involved, e.g., the adult head, lungs, kidneys, etc.

Figure 6:
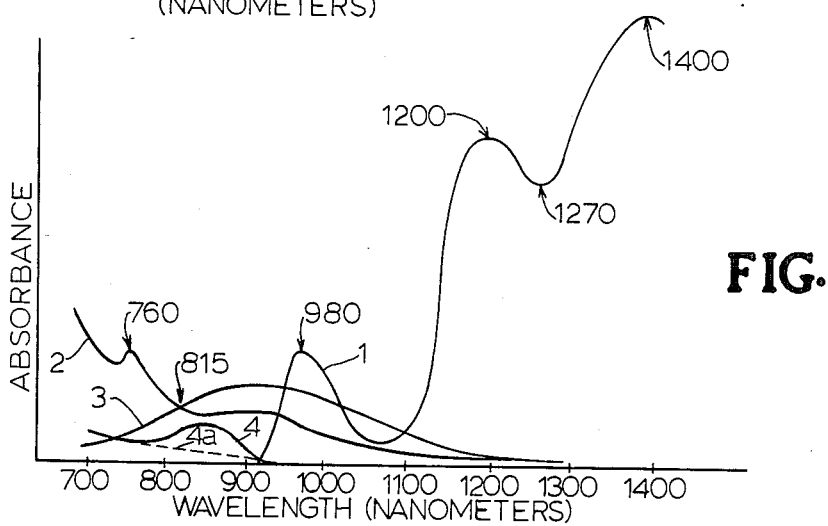
FIG. 6 is a plot of the absorption spectra of water, hemoglobin, oxyhemoglobin, and cytochrome a, $a_3$ over the near-infrared range of about 700 to about 1400 nanometers, illustrating six wavelength values (indicated by arrows) at which absorption measurements are taken in an illustrative system.

The spectra of water (curve 1), hemoglobin (curve 2), and oxyhemoglobin (curve 3) are shown in FIG. 6 in the near infrared spectrum, over the range from about 700 to 1400 nanometers. In addition, the absorption curve of cytochrome $a,a_3$ is illustrated for later discussion. These spectra were obtained by bench-top spectrophotometry using transillumination. The water spectrum is a so-called absolute spectrum, i.e., obtained from a cuvette full of water using an empty cuvette as a "blank" to determine $I_o$ at each wave length. The other spectra are of the hemoglobin and oxyhemoglobin compounds each dissolved in watery solution against a water blank.

In order to make spectrophotometric determinations of the amount of a particular molecular species in a material or body organ of unknown volume and/or unknown optical pathlength, the minimum number of wavelengths required equals the number of absorbing molecular species. Additional wavelengths may be required if the geometry of the input and collection of the photons in the system being measured is complex, or varies from case to case, or if the wavelength dependence of scattering adds significantly differently at the two extremes of the spectral range used. In the following examples increasing levels of complexity will be used as illustrations.

For the sake of simplicity, the first example is restricted to two dilute components of unknown concentration: hemoglobin (Hb; also known as de-oxyhemoglobin) and oxyhemoglobin ($HbO_2$). The environment to be analyzed for these dilute components will be a small body organ (from the size of a finger tip to a baby's head) and the constant media absorber, or "reference component", of known concentration in this example is water. The mode of observation is transillumination, with radiation input and collection (detection) points diametrically across the finger or head. When the absorption curves do not overlap, a four wavelength method can be practical with the tacit implication that the "scattering baseline" is flat, i.e. that for the accuracy required the scattering can be considered wavelength independent.

In FIG. 6, the relative absorption contributions by water and the two hemoglobin species are shown which approximate the normal relative contributions of these three absorbers in the human head. Similarly, the cytochrome $a,a_3$ contribution to the brain absorption is shown in approximate scale (with the oxidized cytochrome $a,a_3$ spectrum shown as curve 4, and the corresponding reduced enzyme spectrum shown as curve 4a), but it should be noted that in the tissues of the finger only a negligible concentration of this enzyme is present.

Considering now the 900 to 1400 nm region of the near infrared spectral range, it is noted that the contributions of hemoglobin become negligible beyond 1150 nm approximately. Thus, the effective optical pathlength through a very small body part such as a finger can be determined by measuring at the trough, at 1270 nm, and at either adjacent peak, i.e. at approximately 1200 or 1400 nm. By subtracting the Absorbance values at the two wavelengths from each other, the differential absorption value is found. When such differential absorption value is divided by the differential absorption (extinction) coefficient for 1 cm of water, the apparent effective pathlength is determined. Assuming an equally flat scattering effect in the adjacent 700 to 900 nm region and with the knowledge that the finger tissues do not contain a measurable amount of cytochrome $a,a_3$ or other species absorbing in this range, it is possible to calculate the exact amounts of the two hemoglobins by transilluminating with any two wavelengths in the 700 to 900 nm range and using the pathlengthening factor established above.

This most simple case is often complicated by a number of factors. In the case of transillumination of a baby's head, for example, the thickness of the baby's head, makes it impractical to use a wavelength such as 1400 nm at which the intensity of the water absorption results in so much light loss that the remaining signal becomes difficult to detect. In this case four wavelengths are chosen in the 900 to 1100 nm range and the absorption intensities are measured. From previous experiments the contributions to the extinction by each absorbing species plus that by the light scattering have been established using approximate models. Best suited for the latter are the corresponding body parts from corpses or appropriate animal models. These may be perfused alternately with hemoglobin-free solution, with oxygen-free blood (for the Hb contribution), and with fully oxygenated blood (for the $HbO_2$ contribution). In the last case a small amount of a poison such as cyanide, that inhibits $O_2$ utilization by the tissue, is added to ensure that the blood remains oxygenated during the observation.

The individual contributions of the three absorbing species and the scattering to the light losses (absorption) in the irradiated environment are then summed at each of the four wavelengths to derive the total absorption equations (referred to herein as "modified Beer-Lambert equations") at each wavelength. These equations take a form as shown below for the 980 nm wavelength:

$$Abs_{980} = x_1 \cdot Hb + x_2 \cdot HbO_2 + z \cdot H_2O + Scatter,$$

wherein $Abs_{980}$ is the Absorbance by the irradiated system of the incident radiation of wavelength 980 nm; Hb, $HbO_2$, and $H_2O$ are the concentrations of hemoglobin, oxyhemoglobin, and water in the irradiated system; and the factors x, y, and z express the relative intensities of the absorption contributions of the associated components. The scattering term ("Scatter") has the factor 1, i.e., its contribution has been normalized. The four wavelengths are chosen so that the three factors x, y, and z will show a considerable range of values. For example, a choice of 940, 980, 1030, and 1070 nm produces a good variation in relative values of the $H_2O$, Hb, and $HbO_2$ contributions.

From this information algorithms are derived by matrix solution of the four unknowns (three absoring component concentrations and the scattering losses) in the four equations. These resulting algorithms take the form $$Hb = a \cdot Abs_{940} + b \cdot Abs_{980} + c \cdot Abs_{1060} + d \cdot Abs_{1100},$$

wherein the values of the constants a, b, c, and d are numerically determined, yielding an expression for the amount of hemoglobin in the system. Similar expressions for $HbO_2$ and $H_2O$ are also obtained. The scattering contribution is not calculated for the algorithms since it is irrelevant to the analytical assessment. The constants a, b, c, etc. can be positive or negative or larger or smaller than unity.

The above described methodology applicable to hemoglobin and oxyhemoglobin concentrations, may be generalized and broadly stated as a spectrophotometric method for quantitatively determining the concentration of a dilute component in an environment containing the dilute component of known identity but of unknown concentration in combination with a reference component of known concentration, in which the following steps are carried out:

(a) directing at the environment incident electromagnetic radiation at a number of wavelengths in a selected spectral region at which the dilute and/or reference components exhibit absorption for the electromagnetic radiation, the number of such wavelengths being determined by the number of dilute and reference components in the environment, and the scattering characteristics of the environment;

(b) determining the absorbance by the environment of the electromagnetic radiation at the various wavelengths and the relative intensities of the absorption contributions of the dilute and reference components and scattering losses from the environment at each of such wavelengths;

(c) at each of the aforementioned wavelengths, establishing absorption equations of the form:

$$Abs_w = \sum_{i=1}^{n} x_i A_i + xR + S$$

wherein: $Abs_w$ is the absorbance by the environment, containing the dilute and reference components, of the incident electromagnetic radiation of wavelength w; $x_i$ is the relative intensity of the absorption contribution of the associated dilute component $A_i$, and wherein terms of the form $x_i A_i$ are set forth for each of the dilute components; n is the number of dilute components; z is the relative intensity of the absorption contribution of the reference component; R is the concentration of the reference component; and S is the normalized scattering of the environment at wavelength w, thereby establishing for each of the aforementioned wavelengths an absorbance equation, to yield a set of simultaneous equations whose number equals the number of dilute and reference components and the number of wavelengths required to characterize the scattering of the environment;

(d) deriving algorithms by matrix solution the aforementioned simultaneous equations, such algorithms being of the form:

$$[c] = \sum_{i=1}^{m} a_i Abs_{w_i},$$

wherein: [c] is the concentration of the specific dilute or reference component; $a_i$ is a determined numerical constant; m is the number of wavelength determinations; and $Abs_{w_i}$ is the absorbance at wavelength w; thereby establishing the concentration of each of the dilute and reference components in the environment.

In the previously described specific example of determining hemoglobin and oxyhemoglobin concentrations, the $H_2O$ signal can be used to provide the pathlengthening factor for concentration calculations. In this manner the amount of Hb and $Hb_2$ can be converted into concentrations in terms of grams per liter. It should be emphasized that this term although a true concentration term refers to an inhomogeneous disperse system. Not only is the hemoglobin contained separately in the red blood cells, the observed water comprises not only the water in the blood plasma but also the water in the cells and lymph spaces. Thus, the concentration units are not directly comparable to the usual ones (grams per 100 ml) used clinically for blood. The latter units can be obtained, however, if we consider only the extra amount of blood that swells the finger with each heartbeat. This pulsatile signal is used for example in the well-known technique of pulse oximetry.

In pulse oximetry, the color of the extra blood that swells the finger with each pulse is determined, i.e., the relative amounts of Hb and $HbO_2$, thus providing a measure of the degree of oxygen saturation of the blood. This technique does not provide information on the total amount of hemoglobin in the blood. Adding a measure of the increase of water with each pulse can be accomplished by using an $H_2O$ absorption signal to measure each pulsatile increase in blood volume in the finger. In this way the actual hemoglobin concentration in the blood can be calculated. The value of this number is general, and not limited to the specific organ (such as the finger) from which it was derived. The hemoglobin content thus determined provides important diagnostic information for such conditions as anemia or polycythemia. In addition, the hemoglobin content is required to determine the actual oxygen content of the blood since most of it is carried combined with hemoglobin in the form of oxyhemoglobin. With the hemoglobin content known and the percent of $O_2$-saturation of the hemoglobin obtained by standard oximetry the much more significant $O_2$-content parameter can be calculated quite simply.

In other organs of larger diameter, e.g. the head, limb musculature, etc., transillumination can be performed as long as the thickness of the tissue does not preclude the acquisition of an instrumentally useful signal after the transmitted radiation has passed through the tissue. In this respect it is to be noted that one cm of water absorbs approximately 80% of the 1400 nm near infrared radiation beamed throught it. Transillumination of an infant's head of 5 cm diameter would show an extinction of approximately 99.97% of the incident near infrared photons by absorption alone. In turbid samples, however, this loss can be increased and overshadowed by losses due to scattering away from the detector and by additional absorption attributable to pathlengthening produced by the multiple scattering encountered by the photons eventually arriving at the detector. Although these light losses are very severe, useful signals have still been derived in such situations. The above example is, however, the limit of the present transillumination technique applied to human organs and body parts.

For application to larger solid organs, a reflectance mode must be employed in lieu of transillumination. As an example of the reflectance mode in application to the adult human head, light may suitably be entered at a first location on the forehead and collected at a second location on the forehead several centimeters distant from the first location, the collected photons having traversed scalp and skull and interacted with the cortical layers of the brain before being scattered out again. In this reflectance mode the crucial need of the present invention is especially clearly illustrated.

Cerebral content of Hb and $HbO_2$ determined by reflectance measurements of radiation intensity can then be referenced to the total water observed, providing a measure of the amount of blood in the brain related to the amount of water encountered by the photon stream from the entry to the collecting points. The blood in the brain is highly compartmentalized in the erythrocites (red blood cells) which are, of course, located in the vascular space. The measured quantities are, however, referred to the total water content, which is present notably in the blood, the brain cells and the meningial spaces, and also to a smaller extent in the bones and skin. The determined concentration therefore is expressed as amounts of Hb (or $HbO_2$) per amount of total "head water" or "tissue water." Most but not nearly all of this tissue water will have been that of the brain and is quite comparable to the water content of other soft tissues. Although this unusual expression appears at first somewhat awkward, in the context of the method of analysis of the present invention it takes on a significance of its own. It should be noted that total water content of tissue and of the brain especially is a quite constant fraction of the total weight and thus such water fulfills the requirement for a spectroscopic "reference component". It should be noted parenthetically that in cases of edema a shift of water from blood and lymphspaces into the cells takes place. In the brain, due to the nonelastic nature of the cranium which forms a pratically closed system, cerebral edema leads to increased intracranial pressure and consequently a forcing out of meningeal fluid and blood. However total intracranial water content remains the same. Incidentally, the loss of hemoglobin compared to the total water signal constitutes an excellent noninvasive indication of intracranial pressure build-up, a potentially fatal affliction.

In the preceding example, absorption by the main oxygen utilizing exzyme cytochrome c oxidase ("cytochrome $a,a_3$" or cyt $a,a_3$") was ignored. In view of this enzyme's relatively small contribution to the overall spectrum the resulting error produced in the hemoglobin data is negligible. In the event, however, that cyt $a,a_3$ information is desired, two more appropriately spaced wavelengths are required, one in the 825 nm region and the other in the 865 nm region. Although a water band does not exist in that exact region the 980 nm peak is relatively near, and hemoglobin which absorbs in both regions can be used as a bridging reference to determine the enzyme concentration.

PREFERRED EMBODIMENTS

Before describing the apparatus that can be utilized to make the measurements referred to above, three caveats should be added to the general principles used in the above example.

The first is the fact that a narrow banded, i.e., relatively monochromatic, light source is an important advantage in constructing incisive algorithms. It is quite clear from FIG. 6 that a photon source providing a narrow band of light, say 5 nm width, will produce much less overlap between absorption characteristics than a broad one, say with a 50 nm spread of wavelengths among its photons.

The second caveat follows directly from the first. When new light sources are used, differing even slightly in center wavelength or in bandwidth, new algorithms must be constructed.

The third caveat is that the practice of the present invention depends strongly on the development of either a means of translating the results in terms of accepted standards, such as spectrophotometric data in clear solutions, or on the de novo development of an extensive data base where accepted standards are not relevant, i.e., in heterogeneous systems such as the brain.

The apparatus system required to make the determination to practice the present invention may suitably comprise the following component systems:

(a) means for producing light of varying wavelengths to enter into the tissue or body part to be characterized for dilute components;

(b) means for detecting light emanating from or reflected from the body part;

(c) means for separating amplifying and otherwise treating the signals obtained from the light source(s) at different wavelengths;

(d) means for calculating the amounts of the absorbing species, using the algorithms derived for these light sources; and (e) means for displaying the results in dimensions of concentrations (i.e., amounts per amount of water or other reference component) or in fractional quantities (such as amount of dilute component in relation to the amount of a reference component other than water in the body part to be measured for determination of the dilute component of unknown concentration).

Figure 7:
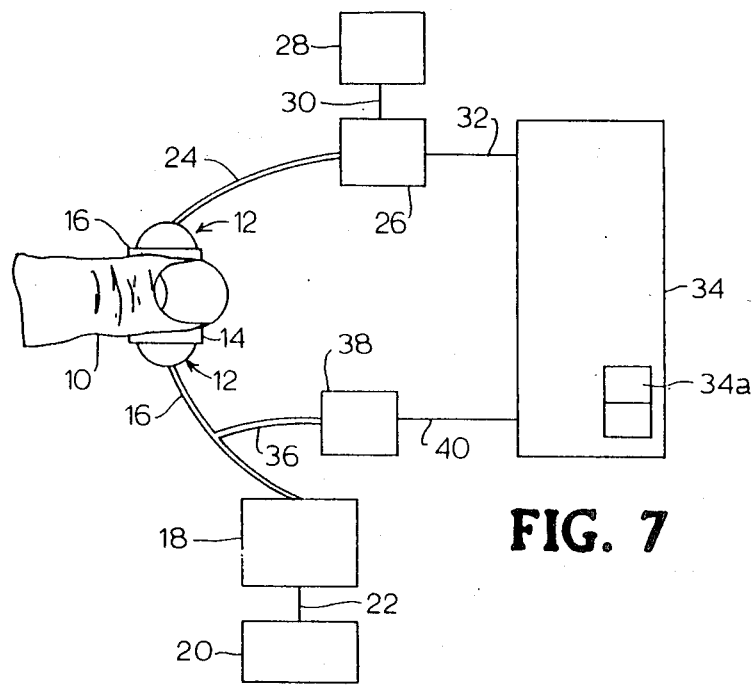
FIG. 7 is a schematic illustration of an apparatus system for in vivo determination of absorbent species in a human finger using transmission.

FIG. 7 is a schematic diagram of a spectrophotmetric system for quantitatively determining the concentration of blood dilute components in a human finger with reference to water contained in the finger.

As previously alluded to, the amount of water encountered by the photons in a body part must be established first. This can be done either by measurements in the spectral range in which water is practically the only absoring species or by multiwavelength differential spectrophotometry if other absorbing species are present. In the human finger water may best be determined by suitable spectrophotometric determinations on fingers of corpses. If such measurements must be made in a region of absorption band overlap with hemoglobin the blood must be replaced by a suitable non-absorbing scattering fluid to mimick the scattering by the red blood cells. Examples of suitable scattering fluids include fluorocarbon blood substitute solutions, calcium carbonate suspensions in saline solution, etc. In such "bloodless" systems, the spectrophotometric characteristics of the corpse fingers may be determined against pure water as a reference standard, to determine the apparent effective optical pathlength for radiation in a given spectral region, as passed through the finger to effect transillumination thereof. By numerous determinations of such type, a database of optical lengths for various types of human fingers (e.g., baby, adolescent, adult; Black, Caucasian, Oriental; etc.) may be developed. In this respect, it is to be noted that melanin is a pigmentation species which is present in varying degrees depending on the race and origins of the human subject. It in some instances may be desirable to treat melanin or other pigmentation-related agents as additional absorbing species in the system and to add further radiation-directing and measurement steps of additional wavelength(s) in determining the concentration of the desired dilute component in the corporeal system under study. Alternatively, routines for data acquisition and alogrithms calculation can be incorporated as software in a microprocessor-based system to provide a set of algorithms appropriate for a given patient at the start of a monitoring period.

Subsequently, the finger of a human test subject may be transilluminated using radiation at various wavelength values, the number of which correspond to the degree of accuracy required in the concentration to be determined for the dilute component of interest. The number of wavelengths at which measurements are made depends, as previously discussed, on the number of absorber species in the system (reference component and dilute component(s)) and the wavelength dependent character of the baseline indicative of scattering losses in the environment being transilluminated or irradiated for reflectance measurements.

From the various absorbance and/or reflectance measurements at the selected wavelengths, a series of simultaneous equations of the type previously discussed are established. After solution by matrix algebra, algorithms are constructed in which the concentration is expressed as the summation of individual absorbance values determined at a given wavelength multiplied by a dimensionless coefficient. Once having determined the amount of the dilute unknown present in the sample (i.e., body organ) this can be ratioed against the water signal to obtain a value in terms of concentration in the total water of the organ.

In another embodiment, total background subtraction can be used to obtain only the increases in blood in a pulsating organ or body part such as the finger, to achieve determination of the concentration in the blood of such bloodborne species, e.g., hemoglobin; waste products such as ammonia, urea, creatinine, and carbon dioxide; substrates and metabolites such as glucose, lipids, and cholesterol; poisons such as carbon monoxide, cyanide, and arsenic; etc.

As applied to the apparatus shown in FIG. 7, the finger 10 has mounted thereon two "optrode" assemblies 12, comprising a source optrode 14 and a collection optrode 16. The direction of transillumination is immaterial: a path through the finger nail may be preferable in certain instances.

The source optrode 14 is connected via optical fiber cable 16 to a light source 18, which in this illustrative embodiment comprises multiple solid state lasers energized by power supply 20 via power supply feedline 22. The laser source 18 emits electromagnetic radiations in the near infrared region, each of a monochromatic character, which are transmitted by the fiber optic cable 16 to the optrode 14 for impingement on the associated surface of finger 10, and transillumination thereof.

The resulting transmitted electromagnetic radiation is collected by the detector optrode 16 and passed via fiber optic cable 24 to an appropriate transducer 26 which in this illustrative embodiment comprises a photomultiplier tube energized by high voltage power supply 28 via power supply feedline 30. The sensed transilluminated signal passing from optical fiber cable 24 to the photomultiplier tube is amplified therein and passed by signal transfer means 32 to the signal processing module 34. In the event that a low voltage powered, "solid state" detector of small size is employed, the detector can be incorporated in the detector optrode. Fiber optic cable 24 is then replaced by an electrical cable directly to the subject.

As shown, the fiber optic cable 16 contains a small separate bundle branch line 36 which transmits a fraction of the monochromatic light from laser source 18 which is directly scattered back by the skin. It is coupled by cable branch line 36 to a photodiode 38, which transmits an electrical signal in signal wire 40 to the calculation module 34, which may for example comprise a digital electronic computer or may comprise a dedicated microprocessor unit or units.

In the computation module 34, the electrical signals transmitted by the photodiode 38 and photomultiplier tube 26 are stored, providing a measure of the incident and detected radiation intensities, together with stored or calculated systems parameters. From these variables and pre-programmed algorithms, or by the aforementioned simultaneous absorbance equations established and solved by matrix solution to yield these algorithms "on line", the concentration(s) of the selected dilute component(s) are calculated and expressed as amounts of such component related to amounts of water or other reference component in the finger system.

In the preferred application of the invention to physiological systems, the successive radiation-directing and measurement steps must be carried out in periods substantially much briefer than the metabolic reaction kinetics of the corporeal environment.

The computation module may continuously provide such concentration data as output through devices 34a comprising suitable meters and/or stripchart recorders, and the like, and store the output concentration data for later access by digital disc recording or similar storage means associated with the computation module.

Figure 8:
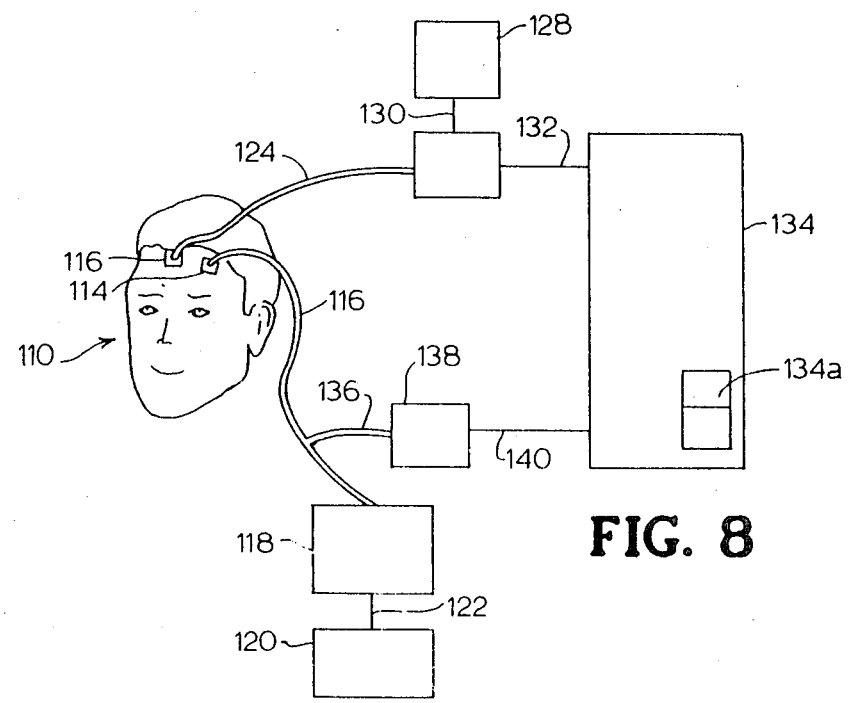
FIG. 8 is a schematic illustration of the reflectance mode used with apparatus of the same general type shown in FIG. 7, in a relatively denser body organ such as an adult's head.

FIG. 8 shows a schematic depiction of a system whose components correspond to those shown in FIG. 7, with the exception of the optrodes 114 and 116, which are arranged for reflectance mode spectrophotometry at spaced-apart regions of the forehead of a human subject 110. All other system elements shown in FIG. 8 system elements are numbered identically to their FIG. 7 counterparts, but with addition of 100 to the reference numerals used in FIG. 7.

In the FIG. 8 system, incident electromagnetic radiation is emitted from optrode 114 and provides photons capable of penetrating both the skin and bone layer as well as the gray matter and white matter of the subject's head. Those photons which are reflected to the optrode 116 are sensed and the resulting detection signal is transmitted by fiber optic cable 124 to the photodetection and calculation module components, as previously described in connection with FIG. 7.

Although the invention has been described with primary reference to the detection and determination of concentrations of dilute components such as tissue components and blood-borne species in body parts (whole tissue/whole organ environments) such as fingers, hands, toes, feet, earlobes, heads, and the like, using near infrared radiation, it will be apparent that the applicability of the invention is not so limited. The method of the invention may be applied to the determination of any dilute component in an environment containing a reference component of known concentration and in any range of the electromagnetic spectrum in which spectophotometric absorbance techniques can be practiced.

Illustrative examples of such alternative applications include but are not limited to, the measurement of acid rain constituents, carbon monoxide, or other air pollution species in atmospheric and oceanic/riparian environments; and the detection of toxic gas species in semiconductor manufacturing operations and industrial gas purification processes.

Further, while the invention has been shown and described with reference to illustrative embodiments, it will be apparent that other variations, modifications and embodiments are possible, and all such apparent variations, modifications and embodiments are to be regarded as being within the spirit and scope of the present invention.

What is claimed is:

1. A spectrophotometric method of quantitatively determining the concentration of a dilute component in an environment containing the dilute component of known identity but of unknown concentration in combination with a reference component of known concentration, by a series of successive, substantially contemporaneous measurements of transmitted and/or reflected radiation at selected wavelengths, comprising:
   (a) determining the apparent effective pathlength in said environment;
   (b) directing at said environment incident electromagnetic radiation of a first wavelength in a selected spectral region at which the dilute and/or reference component(s) exhibit absorption for the electromagnetic radiation;
   (c) measuring the first wavelength radiation transmitted and/or reflected by the environment;
   (d) directing at the environment incident electromagnetic radiation of at least one other wavelength in the selected spectral region at which the dilute and/or reference component(s) exhibit absorption of different relative intensities than for the first wavelength incident radiation;
   (e) measuring the other wavelength radiation transmitted and/or reflected by the environment;
   (f) determining extinction coefficient values for the dilute component at said first and other wavelengths in said environment; and
   (g) based on the apparent effective pathlength determined for the environment, the extinction coefficient values for the dilute component at said first, and other wavelengths, and the measured absorbed and/or reflected radiation at said wavelengths, determining the relative amount of the dilute component to the amount of the reference component, as the concentration of the dilute component in the environment.

2. A method according to claim 1, wherein said apparent effective pathlength of said environment is determined by the steps comprising:
   (i) measuring the absorbance of said reference component at different selected wavelengths in said selected spectral region;
   (ii) calculating the differential absorbance from the measured absorbance values;
   (iii) determining the extinction coefficient values for said reference component at the different selected wavelengths of step (i);
   (iv) calculating the differential extinction coefficient from the determined extinction coefficient values for said reference component; and
   (v) dividing the differential absorbance by the differential extinction coefficient to yield the apparent effective pathlength of said environment.

3. A method according to claim 1, wherein said determination of step (f) is effected by establishing simultaneous modified Beer-Lambert equations for each of said absorption/scattering measurement steps, and solving said equations for the concentrations of said dilute component and said reference component is said environment.

4. A method according to claim 1, wherein a second dilute component of unknown concentration is contained in said environment, and wherein electromagnetic radiation of a third wavelength in said selected spectral region is directed at said environment at which said second dilute component exhibits an absorption for the electromagnetic radiation, and the third wavelength radiation transmitted and/or reflected by the environment is measured, and employed to determine the relative amount of the second dilute component to the amount of the reference component.

5. A method according to claim 4, wherein three simultaneous modified Beer-Lambert equations are established for the concentration of the dilute components and reference component in said environment.

6. A method according to claim 1, wherein said environment effects scattering of said electromagnetic radiation which is independent of wavelength of said radiation, and wherein the transmitted and/or reflected radiation is measured at a single additional wavelength.

7. A method according to claim 1, wherein said environment effects scattering of said electromagnetic radiation to an extent which is of sloped linear relationship to wavelength, and wherein the transmitted and/or reflected radiation is measured at an additional two wavelengths.

8. A method according to claim 1, wherein said environment effects wavelength scattering of said electromagnetic radiation which is a non-linear function of wavelength, and wherein the transmitted and/or reflected radiation is measured at an additional at least three wavelengths.

9. A method according to claim 1, wherein said environment is a corporeal environment.

10. A method according to claim 9, wherein said environment is selected from the group consisting of corporeal tissue and corporeal organs.

11. A method according to claim 9, wherein the dilute component is selected from the group consisting of tissue components and blood-borne species.

12. A method according to claim 9, wherein the dilute component is selected from the group consisting of enzymes, metabolites, substrates, waste products and poisons.

13. A method according to claim 9, wherein the dilute component is selected form the group consisting of glucose, hemoglobin, oxyhemoglobin, and cytochrome $a,a_3$.

14. A method according to claim 9, wherein said corporeal environment comprises a body portion selected from the group consisting of heads, fingers, hands, toes, feet, and earlobes.

15. A method according to claim 9, wherein said reference component is water.

16. A method according to claim 1, wherein said environment comprises an externally added indicator solution as a reference component.

17. A method according to claim 14, wherein said environment is a corporeal corpse body moiety, and said indicator is an aqueous solution of indocyanine green dye.

18. A method according to claim 1, wherein a first dilute component and reference component exhibit absorption for the electromagnetic radiation in said selected spectral region and a second dilute component does not exhibit absorption for the electromagnetic radiation in said spectral region, and wherein the first and second dilute components exhibit absorption for electromagnetic radiation in a second spectral region closely proximate to said selected spectral region and in which the reference component does not exhibit absorption for the electromagnetic radiation, comprising determining the relative amount of the first dilute component to the amount of the reference component in said selected spectral region as the concentration of the first dilute component in the environment, and utilizing the first dilute component whose concentration is thus determined, as a reference component for the second dilute component in said second spectral region.

19. A method according to claim 1, wherein said electromagnetic radiation is infrared radiation having a wavelength in the range of from about 700 to about 1400 nanometers.

20. A method according to claim 1, wherein subsequent to determination of the concentration of the dilute component in the environment, the environment is monitored for changes in said concentration.

21. Apparatus for spectrophotometrically quantitatively determining the concentration of a dilute component in an environment containing the dilute component of known identity but of unknown concentration in combination with a reference component of known concentration, comprising:
(a) means for producing electromagnetic radiation of known wavelengths and directing said radiation into the environment to be characterized for the dilute component;
(b) means for detecting electromagnetic radiation emanating from and/or reflected from the environment and producing therefrom an electrical signal corresponding thereto;
(c) means for receiving said electrical signal and producing therefrom electrical signals corresponding to said different wavelengths;
(d) means receiving and operatively responsive to said electrical signals corresponding to said different wavelengths, to establish absorbance equations responsive to said electrical signals corresponding to said different wavelengths, wherein absorbance at each of the wavelengths is expressed as a function of the relative intensities of the absorption contributions of the dilute and reference components and the concentrations of the dilute and reference components, and for calculating the amounts of the dilute and reference components by solution of said absorbance equations; and
(e) means for displaying the calculated concentrations of said dilute and reference components.

22. A spectrophotometric method of quantitatively determining the concentration of a dilute component in an environment containing the dilute component of known identity but of unknown concentration in combination with a reference component of known concentration, comprising:
(a) directing at the environment incident electromagnetic radiation at a number of wavelengths in a selected spectral region at which the dilute and/or reference components exhibit absorption for the electromagnetic radiation, the number of said wavelengths being determined by the number of dilute and reference components in the environment, and the scattering characteristics of the environment;
(b) determining the absorbance by the environment of the electromagnetic radiation at the various wavelengths and the relative intensities of the absorption contributions of the dilute and reference componets and scattering losses from the environment at each of said wavelengths;
(c) at each of said wavelengths, establishing absorption equations of the form:

$$Abs_w = \sum_{i=1}^{n} x_i A_i + zR + S,$$

wherein: $Abs_w$ is the absorbance by the environment, containing the dilute and reference components, of the incident electromagnetic radiation of wavelength w; $x_i$ is the relative intensity of the absorption contribution of the associated dilute component $A_i$, and wherein terms of the form $x_i A_i$ are set forth for each of the dilute components; n is the number of dilute components; z is the relative intensity of the absorption contribution of the reference component; R is the concentration of the reference component; and S is the normalized scattering of the environment at wavelength w; thereby establishing for each of said wavelengths an absorbance equation, to yield a set of simultaneous equations whose number equals the number of dilute and reference components and the number of wavelengths required to characterize the scattering of the environment;
(d) deriving algorithms by matrix solution of said simultaneous equations, said algorithms being of the form:

$$[c] = \sum_{i=1}^{m} a_i Abs_{wi},$$

wherein: [c] is the concentration of the specific dilute or reference component; $a_i$ is a determined numerical constant; m is the number of said wavelength determinations; $Abs_{wi}$ is the absorbance at wavelength w; thereby establishing the concentration of each of the dilute and reference components in the environment.

23. A method according to claim 22, wherein subsequent to determination of the concentration of each of the dilute and reference components in the environment, the environment is monitored to determine changes in said concentrations.

* * * * *